United States Patent
Carney et al.

(10) Patent No.: US 9,402,771 B2
(45) Date of Patent: Aug. 2, 2016

(54) METHOD AND COMPUTER PROGRAM FOR MONITORING USE OF AN ABSORBENT PRODUCT

(75) Inventors: Joshua Carney, Mölndal (SE); Allan Elfström, Deptford, NJ (US); Mattias Bosaeus, Kållered (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/363,313

(22) PCT Filed: Dec. 21, 2011

(86) PCT No.: PCT/SE2011/051565
§ 371 (c)(1),
(2), (4) Date: Jun. 6, 2014

(87) PCT Pub. No.: WO2013/095230
PCT Pub. Date: Jun. 27, 2013

(65) Prior Publication Data
US 2014/0327546 A1    Nov. 6, 2014

(51) Int. Cl.
*G08B 23/00* (2006.01)
*A61F 13/42* (2006.01)
(Continued)

(52) U.S. Cl.
CPC .............. *A61F 13/42* (2013.01); *G08B 21/182* (2013.01); *G08B 21/20* (2013.01); *A61F 2013/424* (2013.01)

(58) Field of Classification Search
CPC ...... A61F 13/42; G06K 7/0008; G08B 21/22; G08B 21/20; G08B 21/182

USPC .......... 340/573.5, 572.1, 573.1, 686.1, 686.2, 340/604; 604/361, 342; 600/30, 549, 301, 600/584

See application file for complete search history.

(56) References Cited

U.S. PATENT DOCUMENTS

| 4,834,733 A * | 5/1989 | Huntoon et al. .............. 604/361 |
| 5,144,284 A * | 9/1992 | Hammett ................... 340/573.1 |

(Continued)

FOREIGN PATENT DOCUMENTS

| CN | 101472543 A | 7/2009 |
| CN | 102076298 A | 5/2011 |

(Continued)

OTHER PUBLICATIONS

International Search Report (Form PCT/ISA/210) issued on Sep. 18, 2012, by the Swedish Patent Office in International Application No. PCT/SE2011/051558. (5 pages).

(Continued)

*Primary Examiner* — Hoi Lau
(74) *Attorney, Agent, or Firm* — Buchanan Ingersoll & Rooney PC

(57) ABSTRACT

A method for monitoring use of an absorbent product, such as an incontinence pad or a diaper, worn by a wearer, includes registering a movement of the wearer by way of a mobile device having a movement sensing device, evaluating whether the registered movement is indicative of urinary and/or faecal voiding by the wearer, and providing product-related information to the wearer or a caregiver of the wearer based on said evaluation. In this way, the product-wearer or the caregiver can be provided with valuable information related to the use of the product, such as recommendations on when to change the product, displayed on the mobile device or a mobile device of the caregiver.

16 Claims, 3 Drawing Sheets

(51) Int. Cl.
*G08B 21/20* (2006.01)
*G08B 21/18* (2006.01)

(56) References Cited

U.S. PATENT DOCUMENTS

| | | | |
|---|---|---|---|
| 5,416,469 A | 5/1995 | Colling | |
| 5,691,932 A * | 11/1997 | Reiner et al. | 368/10 |
| 5,978,712 A * | 11/1999 | Suda et al. | 607/41 |
| 6,266,557 B1 | 7/2001 | Roe et al. | |
| 6,354,991 B1 * | 3/2002 | Gross et al. | 600/29 |
| 6,617,488 B1 | 9/2003 | Springer et al. | |
| 6,652,449 B1 * | 11/2003 | Gross et al. | 600/30 |
| 7,250,547 B1 * | 7/2007 | Hofmeister et al. | 604/361 |
| 7,700,821 B2 | 4/2010 | Ales, III et al. | |
| 7,737,322 B2 | 6/2010 | Ales, III et al. | |
| 7,855,653 B2 | 12/2010 | Rondoni et al. | |
| 7,977,529 B2 | 7/2011 | Bergman et al. | |
| 8,121,691 B2 | 2/2012 | Gerber et al. | |
| 8,395,014 B2 | 3/2013 | Helmer et al. | |
| 9,224,102 B2 * | 12/2015 | Barda | A61F 13/42 |
| 9,283,123 B2 * | 3/2016 | Lewis | A61F 13/42 |
| 2002/0026164 A1 | 2/2002 | Camarero Roy et al. | |
| 2002/0145526 A1 * | 10/2002 | Friedman et al. | 340/573.5 |
| 2003/0078553 A1 | 4/2003 | Wada et al. | |
| 2004/0055367 A1 | 3/2004 | Swiecicki et al. | |
| 2004/0078014 A1 * | 4/2004 | Shapira | 604/361 |
| 2004/0100376 A1 | 5/2004 | Lye et al. | |
| 2004/0220538 A1 * | 11/2004 | Panopoulos | 604/361 |
| 2004/0230172 A1 * | 11/2004 | Shapira | 604/361 |
| 2005/0033250 A1 * | 2/2005 | Collette et al. | 604/361 |
| 2005/0137542 A1 | 6/2005 | Underhill et al. | |
| 2005/0195085 A1 * | 9/2005 | Cretu-Petra | 340/573.5 |
| 2005/0245839 A1 * | 11/2005 | Stivoric et al. | 600/549 |
| 2006/0064037 A1 | 3/2006 | Shalon et al. | |
| 2007/0142799 A1 * | 6/2007 | Ales et al. | 604/361 |
| 2007/0252713 A1 * | 11/2007 | Rondoni et al. | 340/573.5 |
| 2007/0252714 A1 * | 11/2007 | Rondoni et al. | 340/573.5 |
| 2007/0255176 A1 * | 11/2007 | Rondoni et al. | 600/573 |
| 2007/0270774 A1 | 11/2007 | Bergman et al. | |
| 2008/0052030 A1 | 2/2008 | Olson et al. | |
| 2008/0058740 A1 * | 3/2008 | Sullivan et al. | 604/361 |
| 2008/0074274 A1 | 3/2008 | Hu et al. | |
| 2008/0167535 A1 * | 7/2008 | Stivoric et al. | 600/301 |
| 2008/0266117 A1 * | 10/2008 | Song et al. | 340/573.5 |
| 2008/0300470 A1 | 12/2008 | Gerber et al. | |
| 2008/0300651 A1 * | 12/2008 | Gerber et al. | 607/41 |
| 2009/0062758 A1 * | 3/2009 | Ales et al. | 604/361 |
| 2009/0326417 A1 * | 12/2009 | Ales et al. | 600/584 |
| 2009/0326491 A1 * | 12/2009 | Long et al. | 604/361 |
| 2010/0009713 A1 | 1/2010 | Freer | |
| 2010/0017265 A1 | 1/2010 | Weingarten et al. | |
| 2010/0076254 A1 * | 3/2010 | Jimenez et al. | 600/30 |
| 2010/0098341 A1 | 4/2010 | Ju et al. | |
| 2010/0114046 A1 | 5/2010 | Ales et al. | |
| 2010/0168700 A1 * | 7/2010 | Schmidt et al. | 604/361 |
| 2010/0201524 A1 * | 8/2010 | Gallagher | 340/573.1 |
| 2011/0015496 A1 | 1/2011 | Sherman et al. | |
| 2011/0046571 A1 * | 2/2011 | Waldhorn | 604/246 |
| 2011/0063433 A1 | 3/2011 | Thonhauser | |
| 2011/0125063 A1 | 5/2011 | Shalon et al. | |
| 2011/0183712 A1 | 7/2011 | Eckstein et al. | |
| 2011/0222774 A1 | 9/2011 | Hong et al. | |
| 2011/0243425 A1 | 10/2011 | Maltbie et al. | |
| 2011/0263952 A1 | 10/2011 | Bergman et al. | |
| 2012/0035496 A1 * | 2/2012 | Denison et al. | 600/547 |
| 2012/0040655 A1 | 2/2012 | Larkin | |
| 2012/0157948 A1 * | 6/2012 | Nhan et al. | 604/361 |
| 2012/0220969 A1 * | 8/2012 | Jang et al. | 604/361 |
| 2012/0256750 A1 | 10/2012 | Novak | |
| 2012/0312086 A1 | 12/2012 | Paz et al. | |
| 2013/0018231 A1 * | 1/2013 | Hong et al. | 600/300 |
| 2013/0023786 A1 | 1/2013 | Mani et al. | |
| 2013/0046239 A1 * | 2/2013 | Gonnelli et al. | 604/135 |
| 2013/0110063 A1 * | 5/2013 | Abraham et al. | 604/361 |
| 2013/0110064 A1 | 5/2013 | Richardson | |
| 2013/0303867 A1 * | 11/2013 | Elfstrom et al. | 600/345 |
| 2014/0292520 A1 * | 10/2014 | Carney et al. | 340/573.5 |
| 2014/0301628 A1 | 10/2014 | Carney | |
| 2014/0327546 A1 * | 11/2014 | Carney et al. | 340/573.5 |
| 2014/0333442 A1 | 11/2014 | Carney | |
| 2014/0372177 A1 | 12/2014 | Agami et al. | |
| 2015/0168365 A1 | 6/2015 | Connor | |

FOREIGN PATENT DOCUMENTS

| | | |
|---|---|---|
| DE | 103 26 489 A1 | 1/2005 |
| DE | 10 2006 053 405 A1 | 5/2008 |
| DE | 10 2009 054 097 A1 | 5/2011 |
| EP | 2 175 398 A1 | 4/2010 |
| JP | S62-299264 A | 12/1987 |
| JP | H10-234761 A | 9/1998 |
| JP | 2000-245779 A | 9/2000 |
| JP | 2000-33989 A | 12/2000 |
| JP | 2001-161732 A | 6/2001 |
| JP | 2001-314433 A | 11/2001 |
| JP | 2002-107361 A | 4/2002 |
| JP | 2002-113008 A | 4/2002 |
| JP | 2003-111797 A | 4/2003 |
| JP | 2003-126140 A | 5/2003 |
| JP | 2004-503014 A | 1/2004 |
| JP | 2004-212060 A | 7/2004 |
| JP | 2004-531287 A | 10/2004 |
| JP | 2005-087543 A | 4/2005 |
| JP | 2005-509934 A | 4/2005 |
| JP | 2007-167264 A | 7/2007 |
| JP | 2008-264232 A | 11/2008 |
| WO | WO 01/50996 A1 | 7/2001 |
| WO | 02/03902 A2 | 1/2002 |
| WO | 02/34127 A1 | 5/2002 |
| WO | 02/100292 A2 | 12/2002 |
| WO | 2007/128038 A1 | 11/2007 |
| WO | WO 2008/023289 A1 | 2/2008 |
| WO | WO 2008/038167 A2 | 4/2008 |
| WO | 2008/055991 A2 | 5/2008 |
| WO | WO 2008/147612 A1 | 12/2008 |
| WO | WO 2009/027871 A1 | 12/2008 |
| WO | WO 2010/040430 A1 | 4/2010 |
| WO | WO 2011/008838 A1 | 1/2011 |
| WO | WO 2011/054045 A1 | 5/2011 |
| WO | WO 2011/057723 A1 | 5/2011 |
| WO | WO 2011/080639 A1 | 7/2011 |
| WO | 2011/125003 A1 | 10/2011 |
| WO | WO 2011/126497 A1 | 10/2011 |
| WO | WO 2011/162402 A1 | 12/2011 |

OTHER PUBLICATIONS

Notification of Transmittal of the International Preliminary Report on Patentability (Forms PCT/IPEA/409 and PCT/Separate Sheet/409) issued on Apr. 28, 2014, by the European Patent Office in International Application No. PCT/SE2011/051558. (6 pages).

Communication in cases for which no. other form is applicable (Form PCT/IPEA/424) and Corrected International Preliminary Report on Patentability (Forms PCT/IPEA/409 and PCT/Separate Sheet/409) with Annex pages, issued on May 27, 2014, by the European Patent Office in International Application No. PCT/SE2011/051558. (13 pages).

International Search Report (Form PCT/ISA/210) issued on Sep. 18, 2012, by the Swedish Patent Office in International Application No. PCT/SE2011/051551. (5 pages).

Notification of Transmittal of the International Preliminary Report on Patentability (Forms PCT/IPEA/416, PCT/IPEA/409 and PCT/Separate Sheet/409) issued on Jun. 2, 2014, by the European Patent Office in International Application No. PCT/SE2011/051551. (10 pages).

International Search Report (Form PCT/ISA/210) issued on Sep. 18, 2012, by the Swedish Patent Office in International Application No. PCT/SE2011/051566. (5 pages).

Notification of Transmittal of the International Preliminary Report on Patentability (Forms PCT/IB/373) and the Written Opinion of the International Searching Authority (Form PCT/ISA/237) issued on Jun. 24, 2014, by the International Bureau of WIPO in International Application No. PCT/SE2011/051566. (8 pages).

(56) References Cited

OTHER PUBLICATIONS

The extended European Search Report issued on Oct. 14, 2014, by the European Patent Office in European Patent Application No. 11878154.1-1952. (9 pages).
Wai et al., "Smart Phone Reminder System for Managing Incontinence at Nursing Home," 2011 IEEE 15th International Symposium on Consumer Electronics (ISCE), (Jun. 14-17, 2011), pp. 254-259, Singapore.
The extended European Search Report issued on Mar. 4, 2015, by the European Patent Office in corresponding European Patent Application No. 11878058.4-1906. (4 pages).
Office Action (Notification of the First Office Action) issued on Jan. 6, 2015, by the State Intellectual Property Office (SIPO) of the People's Republic of China in corresponding Chinese Patent Application No. 201180075757.1, and an English Translation of the Office Action. (20 pages).
International Search Report (PCT/ISA/210) mailed on Sep. 14, 2012, by the Swedish Patent Office as the International Searching Authority for International Application No. PCT/SE2011/051565.
International Preliminary Report on Patentability (PCT/IPEA/409) mailed on Feb. 20, 2014 for International Application No. PCT/SE2011/051565 with PCTIPEA/416.
U.S. Appl. No. 14/360,774, Carney.
U.S. Appl. No. 14/361,494, Carney et al.
U.S. Appl. No. 14/362,261, Carney.
Carney, Joshua, U.S. Appl. No. 14/360,774 entitled "Method for Measuring the Absorption of Fluid in an Absorbent Product," filed in the U.S. Patent and Trademark Office May 27, 2014.
Carney, Joshua, et al., U.S. Appl. No. 14/361,494 entitled "Method and Computer Program for Monitoring Use of an Absorbent Product," filed in the U.S. Patent and Trademark Office on May 29, 2014.
Carney, Joshua, U.S. Appl. No. 14/362,261 entitled "Method, Monitoring System and Computer Program for Monitoring Use of an Absorbent Product," filed in the U.S. Patent and Trademark Office on Jun. 2, 2014.
An English Translation of the Office Action (Notice of Reasons for Rejection) issued on Jul. 27, 2015, by the Japanese Patent Office in Japanese Patent Application No. 2014-548726. (4 pages).
An English Translation of the Office Action (Notice of Reasons for Rejection) issued on Aug. 10, 2015, by the Japanese Patent Office in Japanese Patent Application No. 2014-548727. (3 pages).
An English Translation of the Office Action (Notice of Reasons for Rejection) issued on Aug. 10, 2015, by the Japanese Patent Office in Japanese Patent Application No. 2014-548729. (5 pages).
U.S. Appl. No. 14/424,350, Carney et al.
Office Action issued by the U.S. Patent and Trademark Office in the U.S. Appl. No. 14/362,261, mailed May 12, 2015, U.S. Patent and Trademark Office, Alexandria, VA. (26 pages).
Office Action (Patent Examination Report No. 1) issued Apr. 17, 2015 by the Australian Intellectual Property Office in corresponding Australian Patent Application No. 2011383785. (3 pages).
Office Action issued by the U.S. Patent and Trademark Office in the U.S. Appl. No. 14/361,494, mailed Jun. 3, 2015, U.S. Patent and Trademark Office, Alexandria, VA (28 pages).
International Search Report (PCT/ISA/210) mailed on Jul. 4, 2013, by the Swedish Patent Office as the International Searching Authority for International Application No. PCT/SE2012/050910. (5 pages).
Written Opinion (PCT/ISA/237) mailed on Jul. 4, 2013, by the Swedish Patent Office as the International Searching Authority for International Application No. PCT/SE2012/050910. (9 pages).
Written Opinion of the International Preliminary Examining Authority (PCT/IPEA/408) mailed on Aug. 22, 2014, by the European Patent Office as the international Preliminary Examining Authority for International Application No. PCT/SE2012/050910. (7 pages).
International Preliminary Report on Patentability/Annex-Amended Sheets, issued in PCT/SE2012/050910, Jan. 28, 2015, European Patent Office, Berlin, DE (16 pages).
Carney, Joshua, et al., U.S. Appl. No. 14/424,350 entitled "Method and Mobile Applications using Cross-Sharing Database for Monitoring Use of Hygiene Products," filed in the U.S. Patent and Trademark Office on Feb. 26, 2015.
Notice of Allowance and Fee(s) due issued by the U.S. Patent and Trademark Office in the U.S. Appl. No. 14/360,774, mailed Sep. 30, 2015, U.S. Patent and Trademark Office, Alexandria, VA. (11 pages).
Office Action issued by the U.S. Patent and Trademark Office in U.S. Appl. No. 14/360,774, mailed Jul. 7, 2015, U.S. Patent and Trademark Office, Alexandria, VA. (24 pages).
Final Office Action issued by the U.S. Patent and Trademark Office in U.S. Appl. No. 14/361,494, mailed Sep. 21, 2015, U.S. Patent and Trademark Office, Alexandria, VA. (22 pages).
An Examination Report issued on Oct. 14, 2015, by the Colombian Patent Office in Colombia Patent Application No. 14154089. (12 pages).
An Examination Report issued on Oct. 23, 2015, by the Canadian Patent Office in Canadian Patent Application No. 2,857,627. (5 pages).
Final Office Action issued by the U.S. Patent and Trademark Office in U.S. Appl. No. 14/362,261, mailed Nov. 13, 2015, U.S. Patent and Trademark Office, Alexandria, VA. (24 pages).
Office Action issued by the U.S. Patent and Trademark Office in U.S. Appl. No. 14/361,494, mailed Feb. 12, 2016, U.S. Patent and Trademark Office, Alexandria, VA. (25 pages).

* cited by examiner

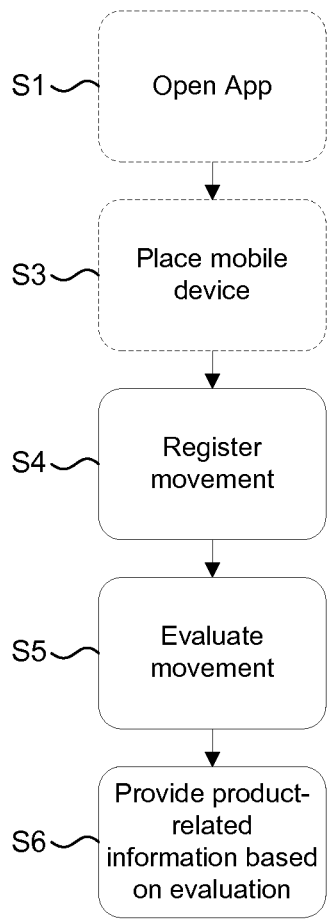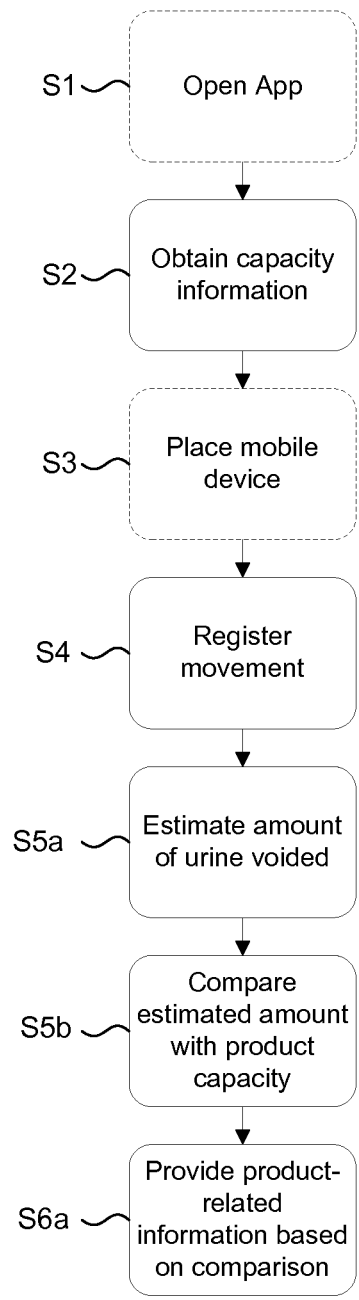
FIG 3
FIG 4

METHOD AND COMPUTER PROGRAM FOR MONITORING USE OF AN ABSORBENT PRODUCT

TECHNICAL FIELD

The present disclosure relates to a method for monitoring use of an absorbent article, a mobile device for carrying out the method, and a computer program for causing the mobile device to carry out the method.

BACKGROUND

Urinary and/or faecal incontinence causes many people to use various types of absorbent products, such as incontinence pads, diapers etc.

Monitoring and timely change of absorbent products may sometimes be difficult, not only when it comes to babies wearing diapers but also when it comes to adults who due to the inability to control the urinary or faecal function find it difficult to know when voiding has taken place and hence when to change the absorbent product. This problem may also concerns people suffering from physical or mental disorders preventing proper monitoring and change of absorbent products. The problem of properly monitoring and timely changing absorbent products is often most apparent during night when the wearer of the product is asleep.

Improper monitoring and change of absorbent products may cause urinary and faecal leakage from the product. To many people suffering from incontinence, this is a huge problem often causing feelings of shame and humiliation.

Several solutions for improved monitoring of use of absorbent articles are known from prior art.

US 2007/0252713 discloses an absorbent sensor pad worn by a patient. One or more sensors that measure urinary voiding parameters are integrally formed in the pad. The sensors may include impedance sensors, strain gauges, temperature sensors, accelerometers, pH sensors, and chemical sensors that measure wetness, volume, temperature, pH, and contents of urine voided by a patient as well as the posture and activity of the patient. The voiding data sensed by the sensors may be stored in a voiding log which may be transmitted to an external device connected to the sensors.

US 2009/0062758 relates to a wetness monitoring system for e.g. a diaper. The system includes a wetness sensor capable of counting the number of discrete insults, and an alarm that is triggered after a critical number of insults, or when a certain period of time has elapsed since the last change of product.

US 2011/0263952 discloses an incontinence management system for monitoring wetness in absorbent articles. The system comprises input for receiving sensor signals indicative of a presence of wetness in an absorbent article and a user interface for communicating with a user of the system.

However, known solutions for monitoring use of absorbent articles often involve complex and expensive products and/or monitoring systems that are not readily available to the public.

SUMMARY

It is an object of the present disclosure to solve or at least mitigate one or more of the above mentioned problems.

In particular, it is an object of the present disclosure to provide a cost efficient and readily available method for monitoring use of absorbent products.

Another object of the present disclosure is to provide a method that can help preventing too late change of absorbent products.

Yet another object of the present disclosure is to provide a method that facilitates care of persons suffering from incontinence.

These and other objects are achieved by a method for monitoring use of an absorbent product, such as an incontinence pad or a diaper, worn by a wearer. The method comprises the steps of registering a movement of the wearer by means of a mobile device comprising a movement sensing device, such as an accelerometer, evaluating whether the registered movement is indicative of urinary and/or faecal voiding by the wearer, and providing product-related information to the wearer or a caregiver of the wearer based on said evaluation.

The present disclosure is intended for monitoring use of an absorbent product worn by a wearer at rest, and in particular for monitoring use of an absorbent product worn by a wearer while sleeping. The present disclosure makes use of the findings that people suffering from incontinence are more inclined to void urine and faeces in light sleep phases. It also makes use of the fact that increased sleep movement is an indication of light sleep. By registering the sleep movement of the person wearing the absorbent product, product-related information that facilitates the use the product can be derived and provided to the wearer of the product or to his caregiver. For example, the product-related information may comprise a recommendation to change the absorbent product, displayed on the mobile device itself, or on a communication device to which the mobile device is communicatively connectable, e.g. a mobile device of the caregiver.

The use of a mobile device, such as a mobile phone, a personal digital assistant (PDA), a tablet computer or any other hand-held computing device that comprises a movement sensing device, such as an accelerometer, makes the method readily available to anyone in possession of such a mobile device. The method is performed by the mobile device through execution of a computer program, which, in a preferred embodiment, is realised in form of an App that is downloadable to a storage medium of the mobile device. By allowing the method to be performed through execution of an App that may be downloaded into existing mobile devices, the method truly becomes readily available to anyone.

In order to carry out the method, the mobile device is placed in a position where it is capable of registering the movements of the person wearing the absorbent product. Preferably, the movement sensing device of the mobile device is an accelerometer that is sensitive enough to register the movement of a sleeping person merely by placing the mobile device in bed next to the sleeping person. For more reliable results, the mobile device may be attached to a wrist band or a belt of the product-wearer, or be carried in a pocket of a pair of pyjamas.

Preferably, the method further comprises the steps of obtaining capacity information related to the capacity of the absorbent product, and providing the product-related information based on both the evaluation of the registered movement and said capacity information. By providing the product-related information based on both the evaluation and the capacity information, the product related information can be based on a relation between the urinary and/or faecal voiding of the product-wearer and the capacity of the product, which allows the product-related information to comprise well-founded recommendations as to the need of changing the product.

To this end, the method may comprise the steps of determining a first parameter indicative of the amount of urine and/or faeces that can be absorbed by the product based on said capacity information, and a second parameter indicative of the amount of urine and/or faeces voided by the wearer based on the registered movement of the wearer. The product-related information is then provided based on a comparison between said first parameter and said second parameter. If the comparison shows that the amount voided by the wearer is close to the capacity of the product, the product-related information can include a recommendation to change the product as soon as possible. If, however, the amount voided by the wearer is well below the capacity of the product, the product-related information may comprise an indication that no change of product is required at this time.

A suitable parameter indicative of the amount of urine and/or faeces voided by the wearer is the number of urinary and/or faecal insults. The number of urinary and/or faecal insults may be determined through the evaluation of the registered movements, as will be discussed in greater detail in the detailed description following hereinafter. Likewise, the parameter indicative of the capacity of the absorbent product may be a maximum number of urinary and/or faecal insults that can be absorbed and/or retained by the product. This allows for easy comparison of the amount voided by the product-wearer and the capacity of the product.

The parameter indicative of the capacity of the product may be determined based on the type of the absorbent product, the absorbency level of the absorbent product, and/or the size of the absorbent product.

Preferably, the product-related information comprises a recommendation to change the product before the voided amount exceeds the amount that can be absorbed and/or retained by the product. However, the product-related information may comprise any of, or any combination of: an indication that no change of product is necessary; an indication that urinary and/or faecal voiding has taken place and that it may be advisable to change the product; a recommendation to change the product; a recommendation to change the product before a certain time; and, a recommendation to exchange the product for another absorbent product having higher or lower capacity than the currently worn product.

The method may further comprise the steps of predicting future insults of urine and/or faeces based on one or more previously registered movements, and to provide the product-related information based also on this prediction.

The product-related information can be provided visually and/or audibly on the mobile device, and/or a communication device to which the mobile device is communicatively connectable, e.g. a mobile device of the caregiver. Preferably, both the content of the product-related information and the way the product-related information is provided to the product-wearer and/or the caregiver is determined based on the evaluation of the registered movement.

As indicated above, the method may be a computer-implemented method performed by a mobile device through execution of a computer program. Thus, according to another aspect of the present disclosure there is provided a computer program for monitoring use of an absorbent product worn by a wearer while sleeping. The computer program is configured to cause a mobile device equipped with a movement sensing device, such as an accelerometer, to perform the method when executed by a processor of the mobile device.

The present disclosure also provides a computer program product comprising a non-volatile memory for storing computer-readable instructions, wherein the above mentioned computer program is encoded on said non-volatile memory.

Furthermore, the present disclosure provides a mobile device for monitoring use of an absorbent product worn by a wearer while sleeping. The mobile device comprises a movement sensing device, such as an accelerometer, a processor, and a storage medium for storing computer programs executable by said processor, which storage medium stores the above mentioned computer program.

BRIEF DESCRIPTION OF THE DRAWINGS

FIG. 3 is a flow chart illustrating the basic principles of the method according to an embodiment.

FIG. 4 is a flow chart illustrating a refined embodiment of the method.

DETAILED DESCRIPTION

Figure 1:
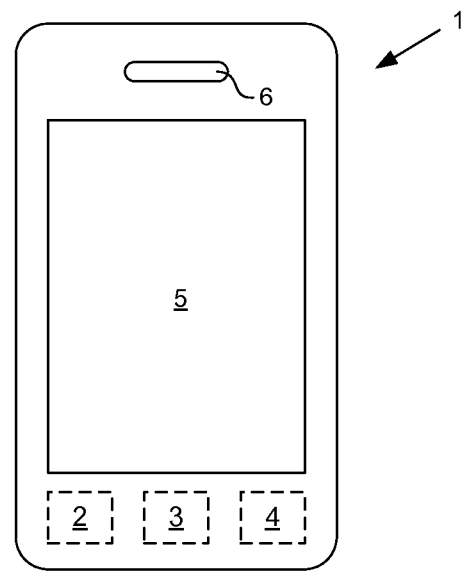
FIG. 1 illustrates a mobile device operable to perform a method according to one embodiment through execution of a computer program.

FIG. 1 illustrates a mobile device 1 for performing the method according to one embodiment. The mobile device 1 in FIG. 1 is a mobile phone in form of what is often referred to as a smartphone but it should be appreciated that the mobile device according to the embodiment may be any type of hand-held computing device, such as a personal digital assistant (PDA) or a tablet computer, devised and configured as set forth below.

The mobile device 1 comprises a movement sensing device 2 in form of an integrated accelerometer for registering motion data indicative of the movement of the mobile device. Such accelerometers are well known in the art and used in many mobile devices of today. The accelerometer 2 is operable to register the movement of a person carrying the mobile device, and preferably also to register the movements of a sleeping person when the mobile device 1 is placed in bed next to the sleeping person. Although the movement sensing device 2 in a preferred embodiment is realised in form of an integrated accelerometer of the mobile device 1, it should be appreciated that other types of movement sensing devices may be used instead or in addition to an accelerometer. For example, the movement sensing device may include a gyroscope of the mobile device 1.

The mobile device 1 further comprises a processor 3 for processing data. The data may be received from communication devices to which the mobile device 1 is communicatively connectable via a network, or stored on a digital storage medium 4 of the mobile device, which storage medium is accessible by the processor 3.

The mobile device 1 is further seen to comprise a display 5 for displaying information to a user, and, if realised in form of a touch-display, also for receiving information from the user in form of user input. The mobile device 1 may also comprise other means for receiving user input, such as buttons, microphones, etc. Furthermore, the mobile device 1 comprises a loudspeaker 6 for outputting sound signals to the user.

The mobile device 1 is operable to perform all method steps of the inventive method, which method steps will be described in more detail below, through execution of a computer program stored in the storage medium 4.

Preferably, the computer program is realised in form of a stand-alone application, meaning that no data has to be received from external devices in order to run the program.

However, the computer program may also be a client application of a distributed software solution further comprising a server-side application residing in an application server to which the mobile device is communicatively connectable. In this case, some of the method steps described below may be performed by the application server through execution of the server-side application.

In a preferred embodiment, the computer program stored on the mobile device 1 is realised in form of an App. An App, sometimes referred to as a mobile app or a mobile application, is a software application specifically designed to run on mobile devices such as smartphones and tablet computers. The App is downloadable into the storage medium 4 from a download server to which the mobile device 1 is connectable. The App may be adapted to a particular mobile operating system, such as Apple iOS, Google Android or Blackberry OS and distributed through known application distribution platforms.

It should thus be appreciated that "the App" hereinafter refers to the computer program stored on the storage medium 4 of the mobile device 1. The App can be executed by means of touching a particular icon displayed on the display 5 of the mobile device 1.

Figure 2:
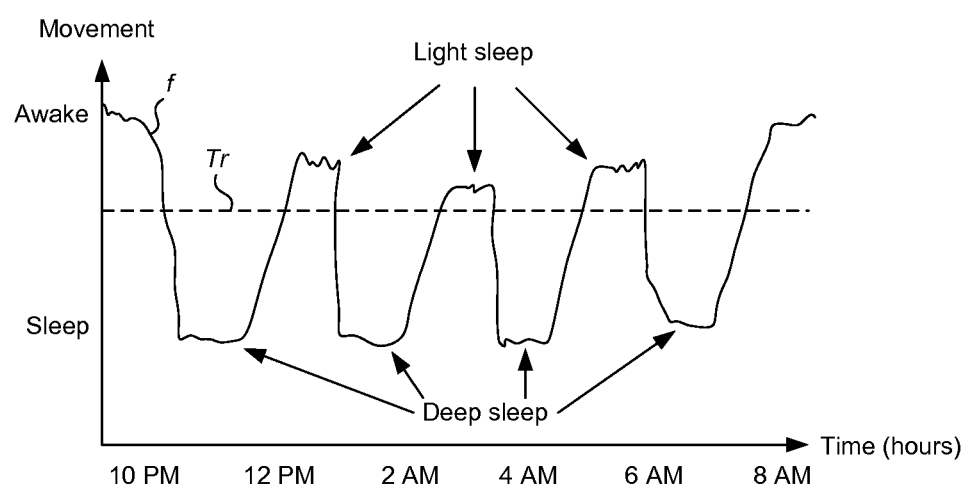
FIG. 2 illustrates data obtained and used by the mobile device when performing the method.

FIG. 2 illustrates a signal f, hereinafter referred to as the awakeness signal, indicative of the movement of a person wearing an absorbent product. The absorbent product may be any type of absorbent personal hygiene article, such as male and female incontinence protectors, sanitary pads, diapers with tape fasteners, pant diapers or belted diapers. The person wearing the absorbent product will hereinafter be referred to as the product-wearer.

The awakeness signal is derived from motion data obtained by the accelerometer 2 of the mobile device 1. The awakeness signal f is hence a function of the motion data obtained by the accelerometer, as will be discussed in greater detail below with reference to FIG. 3. The awakeness signal f is used by the App to determine whether the product-wearer is likely to have voided urine and/or faeces, and, based on this determination, to provide the product-wearer or a caregiver of the product-wearer with recommendations as to the use of the absorbent article, for example a recommendation to change the product for a new one.

In order to obtain the motion data, the mobile device 1 is placed in a position where the accelerometer 2 is capable of registering the movement of the person while sleeping, e.g. under the pillow or mattress, or next to the person in bed.

As illustrated in FIG. 2, the awakeness signal f reveals a decrease in movement around 10 PM, indicating that the person is falling asleep. Between 7 AM and 8 AM an increase in movement is registered, indicating that he person is about to wake up.

During the night, the awakeness signal f indicates that the person experiences a plurality of phases of light sleep, characterised by increased movement. This increase in movement is used by the App to determine the likelihood of urinary and/or faecal voiding by the product-wearer, as described in greater detail below.

Figure 5:
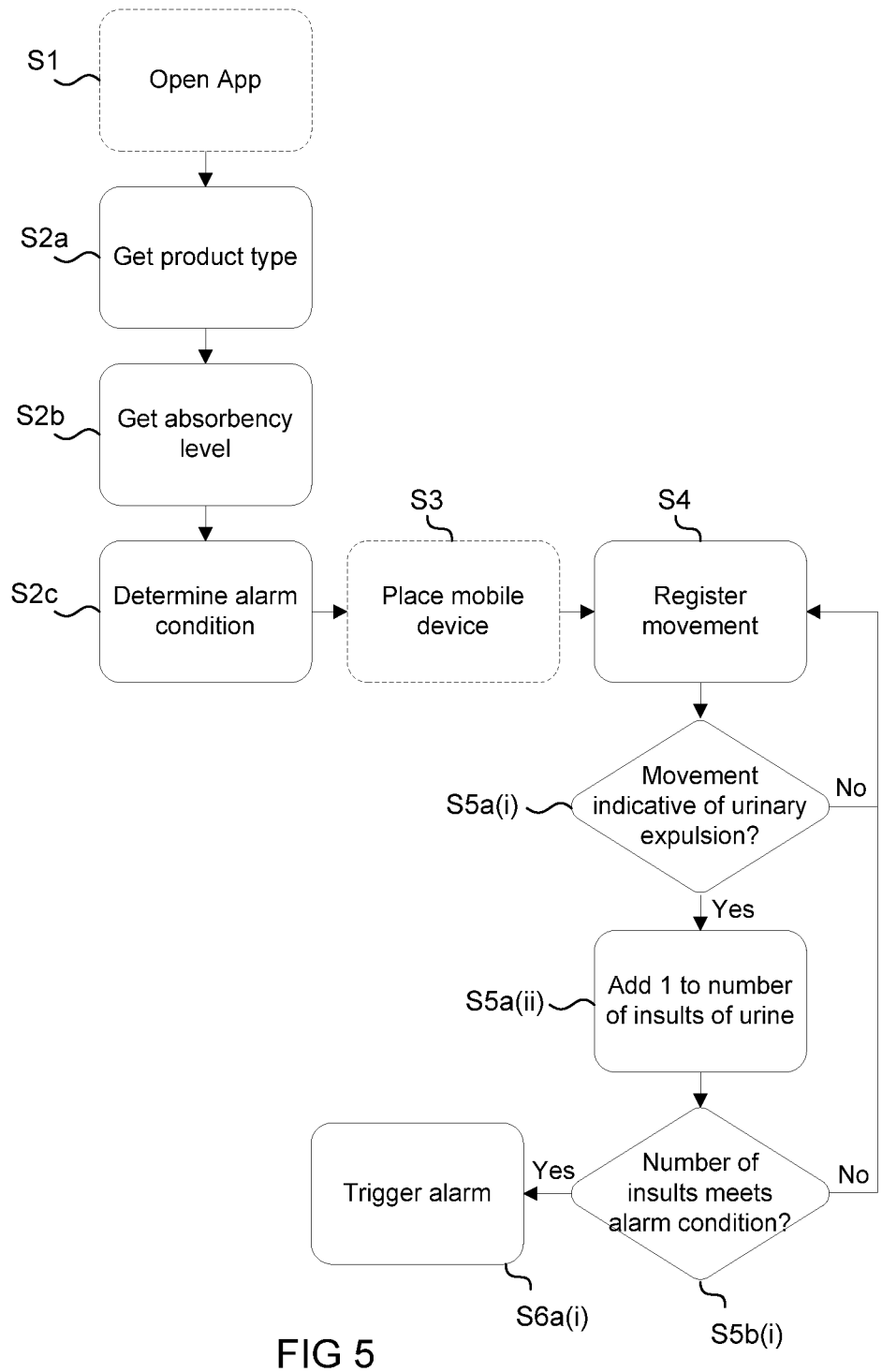
FIG. 5 is a flow chart illustrating an even more refined embodiment of the method.

FIGS. 3 to 5 are flowcharts illustrating different aspects of the inventive method for monitoring use of an absorbent product. In the description of these flowcharts, simultaneous reference will be made to the mobile device 1 in FIG. 1 and the awakeness signal f in FIG. 2. In the flowcharts of FIGS. 3 to 5, boxes drawn with dashed lines indicate method steps performed by a user of the App, while boxes drawn with continuous lines indicate method steps performed by the mobile device 1 through execution of the App.

Although the method will hereinafter be described in the context of urinary voiding by the product-wearer, it should be appreciated that the method is equally applicable in the context of faecal voiding.

FIG. 3 illustrates the basic principles of the inventive method.

In a first step, S1, the App is opened by a user, e.g. the product-wearer himself or his caregiver.

In step S3, the mobile device 1 is placed in a position where the accelerometer 2 of the mobile device is capable of registering the movement of the product-wearer while the product-wearer is asleep.

In step S4, the mobile device 1 registers the movement of the product-wearer by collecting motion data by means of the accelerometer 2.

In step S5, the movement is evaluated by processing the collected motion data. The evaluation is made to determine whether the registered movement is indicative of urinary voiding by the product-wearer.

In step S6, product-related information is provided to the product-wearer and/or his caregiver based on the evaluation in step S5. That the product-related information is provided based on the evaluation means that at least the content of the product-related information is based on the evaluation. Preferably, however, also the way the product-related information is provided to the product-wearer and/or the caregiver is based on the result of the evaluation in step S5.

The product-related information may comprise any of, or any combination of:
  an indication that no change of product is necessary,
  an indication that urinary voiding has taken place and that it may be advisable to change the product,
  a recommendation to change the product,
  a recommendation to change the product before a certain time,
  a recommendation to exchange the product for another absorbent product having higher or lower capacity than the currently worn product.

The product-related information is preferably provided to the product-wearer through visual, audible and/or vibratory signalling on the mobile device 1. Instead, or in addition, it may be provided on a communication device, such as another mobile device or a computer, with which the mobile device 1 can communicate, for example a communication device of a caregiver of the product-wearer. In the latter scenario, the product-related information may be provided to the communication device e.g. in form of a text message (sms) or an e-mail.

The registration step S4 involves collection of motion data in at least one dimension. Preferably, it involves collection of motion data in a plurality of dimension, and even more preferably collection of motion data in three dimensions. To this end, the accelerometer 2 may be configured to detect specific forces in a plurality of directions, e.g. the x, y, and z direction.

The evaluation step S5 may then be performed by analysing the awakeness curve f in FIG. 2. The awakeness curve f may be calculated by the App by performing the following steps:
  Determining at least one reference value for the force sensed in the at least one direction. This reference value is the force sensed by the accelerometer 2 when the mobile device 1 is placed in rest to detect the movement of the product-wearer in step S3, before registration of the movement.
  For a plurality of measurement points, determining a standard deviation from the reference value based on the sensed force. In an exemplary embodiment, 60 measurements are obtained and the standard deviation of the 60 measurement points from the reference value is determined. If motion data is collected in a plurality of directions, the standard deviation from the reference value in the respective direction is calculated, and the standard deviations in the different directions are summed to obtain a standard deviation sum.

Calculating the awakeness curve f as the standard deviation (or, in case of multi-dimensional analysis, the standard deviation sum) as a function of time using known curve fitting techniques.

The functionality for determining whether urinary voiding is likely to have occurred may be implemented in different ways. The basic concept is to detect a "sleep disturbance" and to assume that urinary voiding takes place when such a sleep disturbance is detected. The App is preferably configured to determine a trigger condition and to assume that urinary voiding has taken place when the trigger condition is fulfilled.

For example, the trigger condition may be a certain increase in movement, i.e. a certain change in the derivative of the awakeness curve f. According to another embodiment, the App is configured to determine a trigger condition in form of a threshold value for the standard deviation or the standard deviation sum. Such a threshold value is indicated in FIG. 2 and denoted Tr. Preferably, the App is configured to adapt the trigger condition based on statistical analysis of the registered motion data, and/or user input.

To allow the trigger condition to be adapted based on user input, the App may be configured to allow the user to give feedback on the product-related information provided by the App, e.g. a recommendations on when to change the product. The process of obtaining user feedback may comprise the step of having the user answer to one or more questions before closing the App after use. For example, the App may be configured to display a question like "When where you recommended to change the product?" together with the reply options "too early", "in good time", and "too late", and to use the user feedback to adapt the trigger condition.

It should thus be appreciated that the App, in a basic embodiment, may be configured to determine that the registered movement is indicative of urinary voiding, and to provide product-related information to the product-wearer and/or the caregiver in form of a notification indicating that there might be a need for changing the product.

FIG. 4 illustrates a more refined embodiment of the inventive method. Here the method is seen to comprise an additional step S2 of obtaining capacity information related to the product's capacity to absorb and/or retain urine. This step should be performed prior to registration of the movement of the product-wearer in step S4.

The capacity information may comprise any of, or any combination of the type of the absorbent product, the absorbency level of the absorbent product, and the size of the absorbent product. The capacity information may be obtained from user input and/or reception of information from a server-side application residing on an application server with which the mobile device 1 can communicate.

The App may also be configured to identify the product automatically based on information obtained by a camera and suitable image recognition software, an RFID reader or a barcode scanner of the mobile device 1, and to obtain the capacity information automatically from a product database stored locally on the mobile device 1 or a product database stored on the above mentioned application server. To this end, the absorbent product may be provided with means for facilitating automatic identification thereof, such as a barcode (e.g. a QR code) or an RFID tag.

Furthermore, the method in FIG. 4 is seen to differ from the method in FIG. 3 in that the step of evaluating the movement of the product-wearer comprises a step S5a of estimating the amount of urine voided by the product-wearer.

This is preferably achieved by keeping track of the number of insults of urine. For example, with reference to FIG. 2, the App may be configured to count the number of times the awakeness curve f rises above the threshold value Tr, i.e. to count the number of light sleep phases experienced by the product-wearer throughout the registration period, and to estimate the amount of urine voided by the product-wearer based thereon. That the App is configured to estimate the amount of urine voided by the product-wearer does not necessarily mean that it is configured to estimate a certain volume or weight of urine voided but rather that the App is configured to determine a parameter that is indicative of the amount of urine voided, such as a parameter corresponding to the number of times the registered movement is indicative of urinary voiding.

In a subsequent step S5b, the estimated amount of urine voided by the product-wearer is compared with the capacity of the product, as given by or calculated based on the capacity information obtained in step S2.

In the last step, S6b, the product-related information is provided to the product-wearer and/or the caregiver based on the comparison in step S5b.

The capacity of the product may for example be determined by the App as a maximum number of insults of urine that the absorbent product can absorb, determined based on user input indicating the type and the absorbency level of the absorbent product. For example, if the user has indicated that the absorbent product is a certain type of incontinence pad having an absorbency level 5 on a scale of 1 to 8, the App may use this information to determine that the product can absorb three insults of urine.

Thus, the comparison between the estimated amount of urine voided by the product-wearer and the capacity of the product in step S5b may involve a comparison between the number of detected insults of urine and a maximum number of insults of urine that the absorbent product can absorb. The information content and the way of providing the product-related information may then be adjusted by the App based on the result of the comparison.

This procedure is shown in more detail in FIG. 5, illustrating yet a refined embodiment of the inventive method.

In FIG. 5, the step of obtaining capacity information (step S2 in FIG. 4) is seen to comprise the steps S2a to S2c.

In the first of these steps, S2a, the App gets information about the type of the absorbent product, i.e. information telling the App whether the absorbent product is an incontinence pad, a diaper, etc. The App is preferably configured to display a list of several product types on the display of the mobile device 1, and to obtain the product type information by having the user indicating the correct alternative in the list of product types.

In the second step, S2b, the App gets information about the absorbency level of the absorbent product. Many types of absorbent products, e.g. incontinence pads, are available within a wide range of absorbency levels, and the product's capability to absorb and retain liquid may vary substantially between different absorbency levels. Typically, the absorbency level is the level of the product's absorption capacity on a predefined scale, which level and scale are indicated on the package of the absorbent product. Preferably, the App is configured to display a scale of absorbency levels corresponding to a scale of absorbency levels presented on the package of the absorbency product, and to obtain the absorbency level by having the user indicating the correct absorbency level on the displayed scale.

As mentioned above, the App may also be configured to obtain the product type information and the absorbency level information automatically through automatic identification of the absorbent product by means of a camera (and image recognition software), an RFID reader or a barcode scanner of the mobile device 1.

Based on the product type information and the absorbency level information, the App is configured to determine a parameter that is indicative of the amount of urine that can be absorbed by the absorbent product. This parameter may be calculated by the App based on said information content, or it may be retrieved from a database of the App itself or a database of a server-side application with which the App can communicate, using one or more parameters identifying the product type and the absorbency level as input parameters in the database request.

In this embodiment, the parameter that is indicative of the amount of urine that can be absorbed by the absorbent product is determined by the App as the number of urinary insults that can be absorbed by the product. This parameter will hereinafter be referred to as the Maximum Insults Parameter.

In step S5c, the App determines an alarm condition based on the capacity information obtained in the previous steps. As the name implies, the alarm condition is a condition that should be fulfilled in order for the App to trigger an alarm to the product-wearer or the caregiver. The alarm is here a type of product-related information that serves the purpose of indicating to the product-wearer or the caregiver that the absorbent product should be changed to avoid urinary leakage from the product. In this embodiment, the App is configured to set the alarm condition as a number of detected urinary insults corresponding to the Maximum Insults Parameter, meaning that the alarm will be triggered when the App has detected a number of urinary insults corresponding to the maximum number of insults that can be absorbed by the absorbent product.

When the alarm condition is determined in step S5c, the mobile device 1 is placed in position to register the movement of the product-wearer while sleeping (step S3), and the registration process starts (step S4).

As part of the evaluation of the movement (Step S5 in FIG. 3), the App is configured to count the number of movements that are indicative of urinary voiding by the product-wearer. To this end, the App determines in a step S5a(i) if the registered movement is indicative of urinary voiding and, if so, adds one to the number of detected urinary insults in a step S5a(ii).

In a subsequent step, S5b(i), the App checks whether the number of detected urinary insults meets the alarm condition, i.e. whether the number of registered movements indicating urinary voiding is equal to or higher than the Maximum Insults Parameter.

When the number of detected urinary insults is equal to or higher than the Maximum Insults Parameter, the App proceeds to step S6a(i) and provides the product-related information (step S6 in FIG. 3) to the product-wearer and/or the caregiver in form of an alarm. The alarm may be a signal that is visually and/or audibly provided on the mobile device 1, and/or a text message (sms) or an e-mail that is transmitted from the mobile device 1 to a communication device of the caregiver, as previously described.

According to another aspect of the present disclosure, the method may involve prediction of future insults of urine, i.e. insults not yet detected by the App through evaluation of the registered movement of the product-wearer. Future insults of urine may be predicted based on one or more previously registered movements of the product-wearer and the prediction may be used to provide recommendations as to the use of the absorbent product.

For example, with reference to the awakeness curve f in FIG. 2, the App may be configured to estimate the time of future insults of urine based on one or more previously calculated awakeness curves. The predictions may be used by the App in various ways. For example, the time at which a certain recommendation is provided to the product-wearer and/or the caregiver may be adjusted based on the predicted time of the next insult. The App may for example be configured not to send an alarm indicating that the absorbent product has to be changed if the predicted time of the next insult is after an estimated wake-up time of the product-wearer, as also estimated by the App based on one or more previously registered movements. Moreover, the prediction can be used by the App to provide product-related information including a recommendation on when a future need for changing the product will arise.

Although the method illustrated in FIGS. 3 to 5 has been described in the context of urinary voiding by the product-wearer it should be appreciated that the method is applicable also for faecal voiding by the product-wearer.

In some embodiments, the App may be configured not to make any distinction between urinary and faecal insults. In these embodiments, the App may be configured to assume that some type of insult has occurred when the registered movement of the product-wearer meets a trigger condition, as discussed above. The number of (undefined) insults may then be calculated by the App and compared with the capacity of the product, as also discussed above.

For some absorbent products, however, it may be desirable to distinguish between urinary and faecal insults by the product-wearer. If the absorbent product is a product for absorption of both urine and faeces, e.g. a diaper, the App may be configured to obtain capacity information indicative of the product's capacity to absorb and/or retain urine and faeces, respectively. It may further be configured to estimate both the amount of urine voided by the product-wearer and the amount of faeces voided by the product-wearer based on the evaluation of the registered movement.

In order to do so, the App may be configured to determine a ratio between urinary insults and faecal insults by the product-wearer. In some embodiments, the App may be configured to determine such a ratio based on the product type information. If, for example, the product type information indicates that the product is a diaper intended for babies weighing 5-8 kg, the App may be configured to retrieve ratio information indicating that two out of three insults by a product-wearer in this user category typically are urinary insults, while one out of three typically is a faecal insult. This ratio information may be retrieved from a product database of the App or a server-side application with which the App communicates, as previously described. The ratio information may be used by the App to estimate, from the registered movement of the product-wearer, the number of insults of urine and the number of insults of faeces, respectively. The App may then compare the number of estimated urinary insults with the number of urinary insults that can be absorbed by the product, the number of estimated faecal insults with the number of faecal insults that can be absorbed and/or retained by the product, and/or the total number of insults with a total number of insults that can be absorbed by the product. The product-related information may then be provided to the product-wearer or the caregiver based on some or all of these comparisons. The number of urinary insults, the number of faecal insults, and/or the total number of insults that can be absorbed by the product may also be obtained by the App from said product database. This functionality allows an alarm comprising a recommendation to change the product to be triggered by the App when the number of urinary insults, the number of faecal insults, or the total number of insults, as determined by the App based on the movement of the product-wearer, meets a respective trigger condition.

It is also contemplated that the App may be configured to use different trigger conditions for urinary and faecal insults, meaning that the App is configured to assume that urinary voiding takes place when a first trigger condition is met, and that faecal voiding takes place when a second and different trigger condition is met. As previously mentioned, the App may be configured to adapt the one or more trigger conditions based on registered movements and/or user input, meaning that one or more detection algorithms used to detect urinary and/or faecal voiding based on the registered movement of the product-wearer are adaptive. This makes it possible to tailor the detection of urinary and/or faecal voiding to the movement pattern of different product-wearers.

Furthermore, it should be appreciated that although the present disclosure is particularly intended for monitoring use of an absorbent product worn by a wearer while sleeping, the inventive concept described herein may be applicable also when the product-wearer is awake. It is sometimes hard to say whether a person is awake or asleep and there are states of decreased physical activity where the movement of a product-wearer that is physiologically "awake" can be used to derive information about the use of an absorbent product in the way described herein. Thus, it should be appreciated that the "awakeness curve" f in FIG. 2 rather should be seen as an "alertness curve" that can be used to derive information about the product-wearer's tendency to void urine and/or faeces, even if the product-wearer is more or less awake. The detection of a "sleep disturbance", on which the assumption that urinary and/or faecal voiding takes place relies, should hence be seen as a detection of a change in alertness level of the product-wearer, rather than a detection of a transition between well-defined phases of sleep.

The invention claimed is:

1. A method of using a mobile device comprising a movement sensing device to monitor use of an absorbent product worn by a wearer, comprising:
   obtaining capacity information related to capacity of the absorbent product,
   placing the mobile device in a position wherein the mobile device is capable of detecting movement of the wearer,
   registering, by way of the mobile device, a movement of the wearer,
   evaluating the registered movement to estimate an amount of urine voided by the wearer, and
   providing product-related information to the wearer or a caregiver of the wearer based on both said evaluation and said capacity information,
   wherein the product-related information comprises at least one of:
   an indication that no change of the absorbent product is necessary,
   an indication that urinary voiding has taken place and that it is advisable to change the absorbent product,
   a recommendation to change the absorbent product,
   a recommendation to change the absorbent product before a certain time, and
   a recommendation to exchange the absorbent product for another absorbent product having a higher or lower capacity than the currently worn absorbent product.

2. The method according to claim 1, wherein the evaluating comprises predicting future insults of urine, and wherein product-related information is provided based on said prediction.

3. The method according to claim 2, wherein the predicting of future insults is based on one or more previously registered movements.

4. The method according to claim 1, wherein said product-related information is provided by at least one of visual, audible and vibratory signalling on the mobile device.

5. The method according to claim 1, wherein said product-related information is provided on a communication device to which the mobile device is communicatively connectable.

6. The method according to claim 1, wherein the product-related information comprises a recommendation as to the use of the absorbent product.

7. The method according to claim 1, wherein the product-related information comprises a recommendation of when to change the absorbent product.

8. The method according to claim 1, wherein the product-related information comprises a recommendation to change to another type of absorbent product having another capacity than the worn absorbent product.

9. The method according to claim 1, wherein the absorbent product is an absorbent personal hygiene article.

10. A non-transitory computer readable recording medium storing thereon a program for monitoring use of an absorbent product worn by a wearer, wherein the computer program, when executed by a processor of a mobile device that comprises a movement sensing device, causes the mobile device to perform the method according to claim 1.

11. The mobile device that monitors use of an absorbent product worn by a wearer, the mobile device comprising the movement sensing device, the processor, and the non-transitory computer readable recording medium encoded with the computer program according to claim 10.

12. The method according to claim 9, wherein the absorbent personal hygiene article is one of a male or female incontinence protector, a sanitary pad, a diaper with tape fastener, a pant diaper and a belted diaper.

13. A method for monitoring use of an absorbent product worn by a wearer, comprising:
   obtaining capacity information related to capacity of the absorbent product,
   registering, by way of a mobile device comprising a movement sensing device, a movement of the wearer,
   evaluating whether a registered movement is indicative of urinary and/or faecal voiding by the wearer, and
   providing product-related information to the wearer or a caregiver of the wearer based on both said evaluation and said capacity information,
   wherein the product-related information comprises at least one of:
   an indication that no change of the absorbent product is necessary,
   an indication that urinary voiding has taken place and that it is advisable to change the absorbent product,
   a recommendation to change the absorbent product,
   a recommendation to change the absorbent product before a certain time, and
   a recommendation to exchange the absorbent product for another absorbent product having a higher or lower capacity than the currently worn absorbent product,
   the method further comprising:
   determining, based on said capacity information, a first parameter indicative of an amount of urine and/or faeces that can be absorbed by the absorbent product, determining, based on the registered movement of the wearer, a second parameter indicative of an amount of urine and/or faeces voided by the wearer, comparing said first parameter and said second parameter, and providing said product-related information based on said comparison.

14. The method according to claim 13, wherein the first parameter indicative of the amount that can be absorbed by the absorbent product is determined based on at least one of product type and an absorbency level of the absorbent product.

15. The method according to claim 13, wherein the first parameter corresponds to a number of insults of urine and/or faeces that can be absorbed by the absorbent product, and the second parameter corresponds to a number of urinary and/or faecal insults by the wearer.

16. The method according to claim 13, wherein the product-related information comprises a recommendation to change the absorbent product before the amount voided by the wearer exceeds the amount that can be absorbed by the absorbent product.

\* \* \* \* \*